United States Patent [19]
Roed et al.

[11] Patent Number: 5,326,452
[45] Date of Patent: Jul. 5, 1994

[54] GLASS ELECTRODE

[75] Inventors: Gjerloff Roed, Tastrup; Niels D. Linnet, Birkerod, both of Denmark

[73] Assignee: Radiometer A/S, Copenhagen NV, Denmark

[21] Appl. No.: 917,013

[22] PCT Filed: Feb. 4, 1991

[86] PCT No.: PCT/DK91/00031

§ 371 Date: Oct. 6, 1992

§ 102(e) Date: Oct. 6, 1992

[87] PCT Pub. No.: WO91/12523

PCT Pub. Date: Aug. 22, 1991

[30] Foreign Application Priority Data

Feb. 7, 1990 [DK] Denmark ............... 0312/90

[51] Int. Cl.$^5$ .................................. G01N 27/26
[52] U.S. Cl. ........................ 204/420; 204/419
[58] Field of Search ............... 204/420, 416, 419

[56] References Cited

U.S. PATENT DOCUMENTS

| 3,713,992 | 1/1973 | Akazawa | 204/420 |
|---|---|---|---|
| 3,853,731 | 12/1974 | Gray et al. | 204/420 |
| 4,052,285 | 10/1977 | Dobson | 204/435 |
| 4,133,735 | 1/1979 | Afromowitz et al. | 204/416 |
| 4,458,685 | 7/1984 | Hiramoto et al. | 204/420 |
| 4,632,732 | 12/1986 | Fog et al. | 204/416 |
| 4,836,907 | 6/1989 | Pederson | 204/415 |

FOREIGN PATENT DOCUMENTS

| 151918 | 9/1983 | Denmark . |
| 0092644 | 11/1983 | European Pat. Off. . |
| 3607522 | 3/1986 | Fed. Rep. of Germany . |
| 2073891 | 12/1983 | United Kingdom . |

OTHER PUBLICATIONS

Rompps Chemie-Lexikon, 8th Edition (1985) p. 1491.

*Primary Examiner*—John Niebling
*Assistant Examiner*—Bruce F. Bell
*Attorney, Agent, or Firm*—David M. Klein; Bryan Cave

[57] ABSTRACT

The glass electrode comprises a membrane of ion sensitive glass. The membrane comprises a composite material consisting of a matrix of ion sensitive glass and a dispersed filling material therein having higher tensile strength than the matrix. The membrane of the glass electrode is particularly resistant to mechanical stress and the glass electrode is i.a. applicable in a tc Pco$_2$ electrode of the Severinghaus-type.

20 Claims, 2 Drawing Sheets

GLASS ELECTRODE

This invention relates to a glass electrode having a membrane of ion sensitive glass characterized with a dispersed filling material therein.

Glass electrodes have been known since the beginning of this century and are i.e. briefly described in RÖPPS Chemie-Lexicon, 8th edition (1985) page 1491. A glass electrode comprises i.e. a very thin membrane of ion sensitive glass. The thin membrane is extremely fragile and gradually many attempts have been made in order to develop more rugged glass electrodes. These more rugged glass electrodes are primarily of the solid state type meaning that the ion sensitive glass is supported by a solid material, for example a metal, an electrically conductive glass and/or a ceramic material. Traditional glass electrodes, on the contrary, have an Unsupported glass membrane which separates an inner liquid and the environments.

Applicant has described glass electrodes of the solid state type in the specifications of British Patent No. GB 2073891, U.S. Pat. No. 4,632,732 and Danish Patent No. DK 151918, respectively. Other descriptions of glass electrodes of the solid state type are found in U.S. Pat. No. 4,133,735 (Afromowitz); in U.S. Pat. No. 4,458,685 (Sumitomo), respectively and in a number of earlier patent specifications, for example U.S. Pat. No. 3,853,731 (Owens-Illinois). The contents of the patent specifications stated above are considered incorporated into the present application by reference.

Further improvement on the strength of the glass membrane is, however, still required and the purpose of the invention is, therefore, to provide such a further improved glass electrode. This is achieved by the glass electrode of the present invention.

The glass electrode according to the invention may depending on the ion sensitive glass employed to the membrane be applied for determination of any ion which can be determined by a glass electrode. These ions are especially $H^+$ or other cations such as alkaline metal cations, alkaline earth metal cations and certain organic cations, for example $Li^+$, $Na^+$, $K^+$, $Rb^+$, $Cs^+$, $NH_4^+$ and $Ag^+$. In a preferred embodiment of the invention the ion sensitive glass is a pH sensitive glass.

The glass electrode according to the invention comprises a filling material with higher tensile strength than the matrix of ion sensitive glass, preferably a filling material with considerably higher tensile strength than the matrix. In this respect considerably higher tensile strength means twice the tensile strength or more, particularly about five times as high tensile strength (measured as bending tensile strength). Typically, a suitable filling material has tensile strength of 200–1000 MPa, especially approx. 500 MPa whereas the matrix has tensile strength of approx. 100 MPa. The filling material lies as a separate phase in the matrix.

Due to high temperature processes in the manufacturing of glass electrodes it is preferred that the filling material has a thermal expansion coefficient which is compatible with the thermal expansion coefficient for the ion sensitive glass. Hereby the tensions are reduced and consequently development of cracks in the product. In practice this is considered the case when the thermal expansion coefficient of the filling material ranges within the thermal expansion coefficient ±20% of the ion sensitive glass.

In order to ensure a massive, pinhole-free structure of the membrane of filling material-containing ion sensitive glass the filling material should be able to enter into intimate connection with the glass phase. Other criterions for the selection of filling material are that the filling material must not affect the ion sensitivity of the glass and must be chemically inert to the frequently occurring test solutions the ion content of which is to be determined, and further that the filling material must not show redox sensitivity. If the criterions mentioned above are fulfilled it will be possible to maintain the same measuring qualities for the electrodes according to the invention as for similar electrodes with no filling material in the ion sensitive membrane.

Suitable filling materials may in all probability be found particularly among inorganic solids which do not decompose at the temperatures of the membrane manufacturing processes, for example oxides, carbides, nitrides, silicates or combinations thereof. A particularly suitable filling material is $ZrO_2$. In addition to this, oxides of Nb and Ti are considered especially interesting potential filling material candidates.

The dispersed phase of the filling material may be formed in situ at controlled cooling down of a melt of ion sensitive glass.

It is preferred that the filling material is a powdered filling material having a maximum grain size less or similar to the membrane thickness, typically less than 1000 $\mu$m, preferably less than 150 $\mu$m and particularly 30–40 $\mu$m.

Further, it is preferred that the ratio between the ion sensitive glass and dispersed filling material in the membrane ranges from 100:1–1:1, preferably 20:1–2:1 and especially 15:1–3:1 (weight basis).

A particularly rugged glass electrode is characterized in that an inner reference electrode is electrically connected to the membrane surface via an electrically conductive solid state connection.

Preferably, the solid state connection comprises a body of electron conductive glass between a metallic conductor and the ion sensitive filling material-containing glass membrane. Such preferred electrodes according to the invention have as stable and reproducible potential and as stable and reproducible sensitivity as common liquid-filled glass electrodes.

Further, the solid state connection comprises preferably a metal layer obtained by thick film technology printed on a ceramic carrier between the ion sensitive filling material-containing glass membrane and a metallic inner reference electrode. In a preferred embodiment said metal layer is located between the above-mentioned body of electron conductive glass and the metallic inner reference electrode. The metal layer is preferably composed of a body of noble metal, especially a platinum body or layer due to platinum's inertness to the electrode glass.

A particularly preferred application of the glass electrode according to the invention is in a $P_{CO_2}$ electrode intended for transcutaneous measuring of $P_{CO_2}$. Said electrodes are applied in intensive care units at hospitals, i.e. outside normal laboratory environment, and consequently the electrodes are required to be as rugged as possible.

The invention will now be further described in connection with the drawing where

BRIEF DESCRIPTION OF THE DRAWINGS

In the figures identical parts are provided with identical reference numerals.

DESCRIPTION OF THE PREFERRED EMBODIMENT

Figure 1:
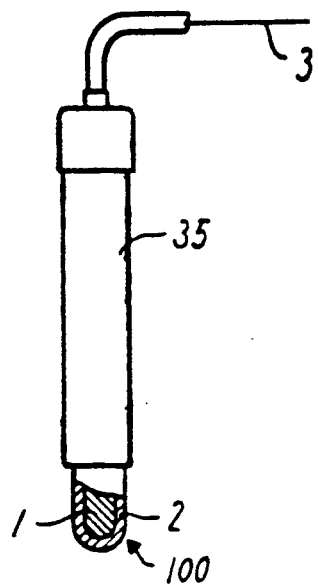
FIG. 1 is a sectional view through a first embodiment of a glass electrode according to the invention.

The embodiment shown in FIG. 1 for the glass electrode according to the invention has an ion sensitive tip 100 which i.a. comprises a metal rod i produced from a Fe alloy containing 25% Cr; 5% Ni and 1% Mo and delivered by Avesta, Copenhagen, Denmark designated 25-5-1L. The major part of the surface of the metal rod 1 is covered by a coherent layer 2 of a pH sensitive glass in which a filling material is dispersed in the form of small particles of $ZrO_2$. The pH sensitive glass is a glass of the type Corning 015 delivered by CORNING GLASS WORKS, Corning, New York, USA having the composition 21.4% $Na_2O$; 6.4% CaO, and 72.2% $SiO_2$ (mole basis). The $ZrO_2$ particles consist of a powdered $ZrO_2$ delivered by MERCK, Darmstadt, West Germany under the trade name zirkon(IV)-oxid, wasserfrei, SELECTIPUR ™. The particles are characterized in that 10% have a grain size less than 10 $\mu$m and 95% have a grain size less than 30 $\mu$m. The ratio between filling material and pH sensitive glass is 15:100 (weight basis).

The ion sensitive tip 100 is supported by a lead glass tube 35 in which an electrical conductor 3 forms connection to the metal rod 1. The connection between the conductor 3 and the metal rod 1 is not shown here as the establishment of said connection is considered known to the worker skilled in the art.

Figure 2:
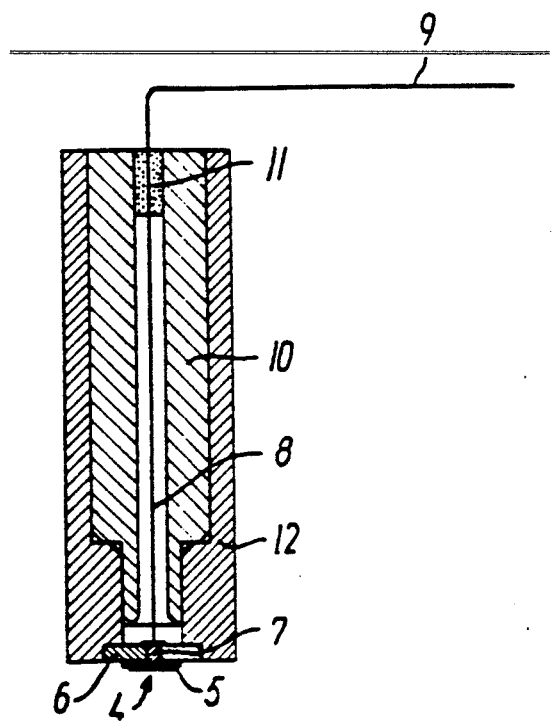
FIG. 2 a sectional view through a second embodiment of a glass electrode according to the invention.
Figure 4:
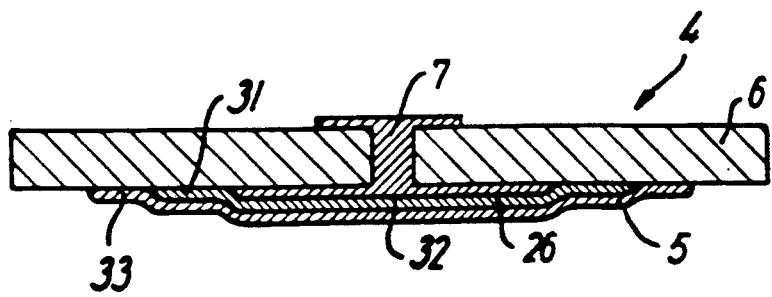
FIG. 4 a section showing in detail the construction of an element comprising an ion sensitive glass membrane and said membrane's support.

The embodiment shown in FIG. 2 for the glass electrode according to the invention has by its front an element 4 comprising a layer 5 facing the environments of filling material-containing pH sensitive glass supported by a ceramic disc 6. Centrally in the ceramic disc 6 is provided a through-going conductor 7 which by its rear is connected to an Ag rod 8 and by its front via a not-shown intermediate layer of electron conductive glass, which is further described below in connection with FIG. 4, is electrically connected to the layer 5. The Ag rod 8 is by its rear connected to a conductor 9 in a not-shown electrode cable. The element 4 is glued into one end of a tubular plastic house 12. In the tubular plastic house 12 is provided another tubular plastic element 10. An epoxy deposit which is provided by the rear of the plastic element 10 serves to maintain and electrically isolate the Ag rod 8 and its not-shown junction to the conductor 9.

Figure 3:
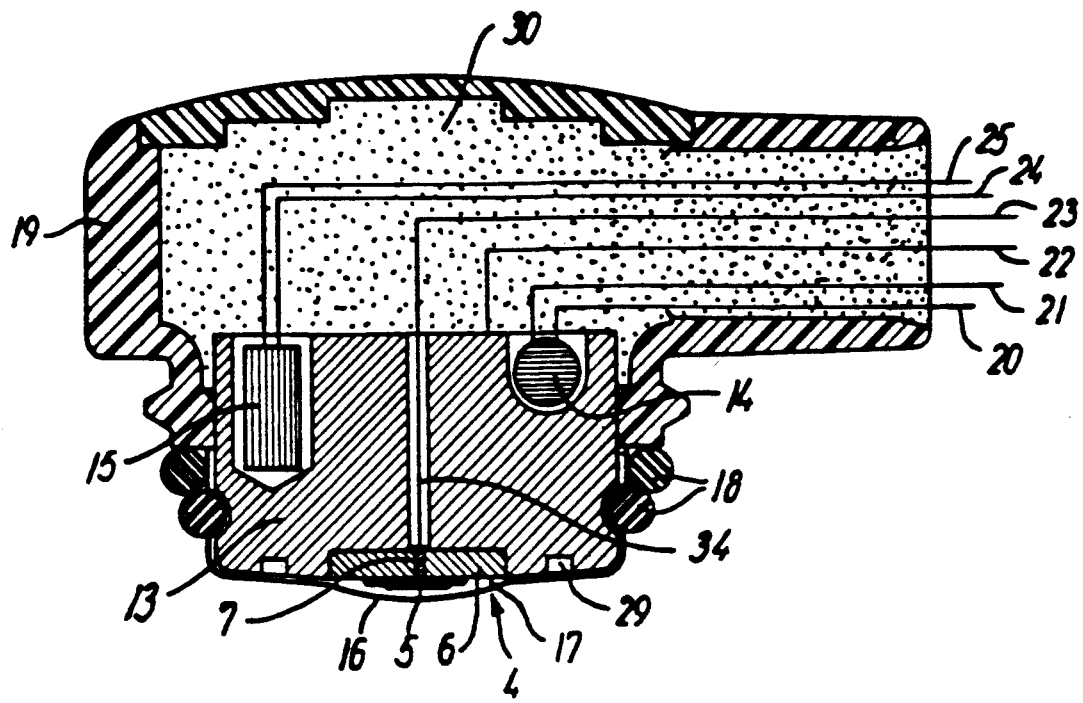
FIG. 3 a sectional view through a third embodiment of a glass electrode according to the invention applied in a $P_{CO_2}$ electrode of the Severinghaus-type.

In the embodiment of FIG. 3 for the glass electrode according to the invention this forms part of a thermostated $P_{CO_2}$ electrode of the Severinghaus-type intended to transcutaneous $P_{CO_2}$ measuring. Said type of electrode is i.a. described in applicant's U.S. Pat. No. 4,836,907.

The glass electrode comprises an element 4 of the type described above in connection with FIG. 2 and more detailed in connection with FIG. 4. The element 4 is glued into a body 13. The conductor 7 in the element 4 is connected with a rod 34 which by its other end is connected to a conductor 23 in a not-shown electrode cable. A heating element 14 in the form of a zener diode and a heat sensor 15 in the form of an NTC-resistor have also been inserted into the silver body 13. Conductors 20, 21, 24 and 25 make electrical connections to the heating element 14 and the heat sensor 15, respectively.

A carbon dioxide permeable polymeric membrane 16 of the type described in applicant's U.S. Pat. No. 4,836,907 mentioned above is mounted in front of the silver body 16. The membrane 16 is maintained on the silver body 13 by means of O-rings 18. A bicarbonate-containing pH-buffer is provided in the chamber 17 between the membrane 16 and the silver body 18.

The silver body 13 is on the surface facing the chamber 17 chlorinated and via its rear connected to a conductor 22 in the not-shown electrode cable. The silver body serves as reference electrode for the pH electrode comprising the element 4 and its connections.

The silver body 13 is glued into a plastic house 19 and the internal of the house is filled with epoxy resin 30.

FIG. 4 shows the element 4 in further detail. The element comprises a disc 6 of the ceramic material forsterite ($2MgO.SiO_2$), for example delivered by Kyocera, Kyoto, Japan. In order to illustrate the dimensions of the element it should be mentioned that the ceramic disc 6 is circular with a diameter of 4 mm and a height of 0.635 mm. A perforation is provided centrally in the disc with a diameter of 0.1 mm. By thick film technique is provided an electrically conductive material 7 on the opposite surfaces of the disc 6 and in the perforation. Said conductive material is provided by printing and burning of Pt-paste, for example of the type 1308A delivered by Demetron, Hanau, West Germany or the type ESL 5542 delivered by ESL Europe, Agmet Ltd., Reading, England.

An approx. 30 $\mu$m thick layer of electron conductive glass 26 is provided by thick film technique so that it fully covers the part 32 of the uncovered surface of the conductive material 7 which is located at one side of the disc 6. The electron conductive glass is in an annular area 31, which surrounds the surface part 32, in direct contact with the disc 6. The electron conductive glass is an $Fe_2O_3$-containing sodium silicate glass. $Fe_2O_3$ (magnetite) is found partly dissolved in the glass phase and partly in the form of solid magnetite crystals distributed in the glass phase. In order to bring the glass into a form suitable for thick film processing the magnetite-containing glass is prior to application crushed into a particle size of typically less than 40 $\mu$m and mixed with such an amount of organic binder of the type ESL 400 delivered by the above-mentioned ESL Europe that a paste having an appropriate consistency for thick film printing is produced.

On the surface of the layer of electron conductive glass 26 turning away from the disc—also by thick film technique—is provided an approx. 35 $\mu$m thick layer of filling material-containing sensitive glass 5. The ion sensitive glass is in an annular area 33 in direct contact with the disc 6. The ion sensitive glass has the same composition as stated in connection with FIG. 1. In order to bring the glass into a form suitable for thick film processing the glass is prior to the application crushed into a particle size of typically less than 40 $\mu$m and together with ZrO$_2$-particles of the type mentioned in connection with FIG. 1 mixed with such an amount of an organic binder of the above-mentioned type ESL 400 that a paste having an appropriate consistency is produced.

The forsterite disc 6, the electron conductive glass 6, and the filling material-containing ion sensitive glass 5 have compatible thermal expansion coefficients all ranging from $10.10^{-6}$–$12.10^{-6}$ °C$^{-1}$. Compatible thermal expansion coefficients is a requisite condition that the materials may be applied together in high temperature manufacturing processes, such as processes involving application of melted glass or burning of a glass paste. A detailed description of manufacturing of ion sensitive electrodes by thick film technique is stated in the above-mentioned U.S. Pat. No. 4,133,735.

Comparative tests among electrodes according to the invention of the type shown in FIG. 2 and corresponding electrodes—except that the layer 5 instead of filling material-containing ion sensitive glass comprises a similar glass without filling material—have been carried through.

The electrodes according to the invention proved remarkably more resistant to mechanical stress, for example scratching of the ion sensitive membrane than the comparative electrodes. As development of cracks in the ion sensitive membrane i.a. owing to mechanical stress is a frequently occurring defect and means that such cracked electrodes must be discarded it is considered an essential improvement being able to reduce or eliminate the development of cracks.

For example, the resistance to scratching has been tested by rubbing the ion sensitive membrane with a polishing cushion of the type DUR delivered by Struers, Copenhagen, Denmark under the trade name TRADU furnished with a coating of diamond powder having a more specific grain size. Tests with grain sizes 3 μm, 6 μm, 9 μm, 25 μm and 45 μm were carried through. The diamond powder was delivered by the above-mentioned firm Struers designated SPRET, SPRIX, SPRAC, SPRAM and SPRIR and was applied to the polishing cushion by spray.

The electrodes according to the invention stood rubbing with a 45 μm diamond powder whereas the comparative electrodes developed cracks (after standing in water overnight) after rubbing with diamond powder with the grain size 6–9 μm.

Another test which documents the resistance to scratching consisted in scratching the ion sensitive membrane with a diamond pick-up with a tip having a curvature radius of 0.050 mm. The diamond was loaded with a well-defined load and tests with various loads were carried through.

The electrodes according to the invention stood scratching by a load of 42 g whereas the comparative electrodes already developed cracks (after standing in water overnight) after exposure to a load of 11 g.

With respect to measuring qualities there was no difference among the electrodes according to the invention and the comparative electrodes.

We claim:
1. A glass electrode which comprises:
a membrane of ion sensitive glass which comprises a composite material comprising a matrix of ion sensitive glass and an inorganic solid filling material in a separate phase dispersed in said matrix, said filling material having a higher tensile strength than said matrix, said membrane of ion sensitive glass with said filling material having improved strength.

2. Glass electrode according to claim 1, characterized in that the ion sensitive glass is a pH sensitive glass.

3. Glass electrode according to claim 2, characterized in that the electrode further comprises a $CO_2$—permeable polymeric membrane located in front of the membrane of ion sensitive glass and that a bicarbonate-containing pH-buffer is enclosed between the two membranes.

4. Glass electrode according to claim 3, characterized in that the electrode further comprises means for heating and thermostating the electrode to a temperature within the temperature range of 37°–44° C.

5. Glass electrode according to claim 1 characterized in that the filling material has a thermal expansion coefficient which is compatible with the thermal expansion coefficient of the ion sensitive glass.

6. Glass electrode according to claim 1, characterized in that the filling material is $ZrO_2$.

7. Glass electrode according to claim 1 wherein said filling material has a maximum grain size less than or substantially the same as the membrane thickness.

8. Glass electrode according to claim 7 wherein said grain size is less than 100 μm.

9. Glass electrode according to claim 7 wherein said grain size is less than 150 μm.

10. Glass electrode according to claim 7 wherein said grain size is 30–40 μm.

11. Glass electrode according to claim 1 wherein the ratio between said ion sensitive glass and said dispersed filling material ranges from 100:1–1:1 by weight.

12. Glass electrode according to claim 11 wherein said ratio is in the range 20:1–2:1.

13. Glass electrode according to claim 11 wherein said ratio is in the range 15:1–3:1.

14. Glass electrode according to claim 1 characterized in that an inner reference electrode is electrically connected to the membrane surface via an electrically conductive solid state connection.

15. Glass electrode according to claim 14, characterized in that the solid state connection comprises a body of electron conductive glass.

16. Glass electrode according to claim 15 characterized in that the ion sensitive glass membrane and the solid state connection are formed as layers on a thick film substrate the solid state connection being embedded between the glass membrane and the thick film substrate.

17. Glass electrode according to claim 14, characterized in that the solid state connection comprises a Pt-body.

18. A Severinghaus $P_{CO_2}$ electrode which comprises a glass electrode according to claim 1.

19. A $P_{CO_2}$ electrode according to claim 18 wherein the $P_{CO_2}$ electrode comprises means for heating and thermostating the electrode to a temperature within the temperature range of 37°–44° C.

20. Glass electrode according to claim 1 wherein said inorganic solid is selected from the group consisting of oxides, carbides, nitrides, silicates, or combination thereof.

* * * * *

UNITED STATES PATENT AND TRADEMARK OFFICE
CERTIFICATE OF CORRECTION

PATENT NO. : 5,326,452

DATED : July 5, 1994

INVENTOR(S): Gjerloff Roed et al.

It is certified that error appears in the above-identified patent and that said Letters Patent is hereby corrected as shown below:

Column 6:

Claim 8, line 2: Delete "100" and insert --1000--.

Signed and Sealed this

Twentieth Day of September, 1994

Attest:

BRUCE LEHMAN

*Attesting Officer*      *Commissioner of Patents and Trademarks*